United States Patent [19]

Kauth et al.

[11] Patent Number: 4,796,381

[45] Date of Patent: Jan. 10, 1989

[54] INSECTICIDAL COMPOSITIONS

[75] Inventors: Hans-Herbert Kauth, Ingelheim am Rhein; Hanshelmut Itzel, Gau-Algesheim, both of Fed. Rep. of Germany

[73] Assignee: Celamerck GmbH & Co. KG, Ingelheim am Rhein, Fed. Rep. of Germany

[21] Appl. No.: 54,437

[22] Filed: May 27, 1987

Related U.S. Application Data

[63] Continuation of Ser. No. 901,019, Aug. 28, 1986, abandoned.

[30] Foreign Application Priority Data

Sep. 6, 1985 [DE] Fed. Rep. of Germany ....... 3531795

[51] Int. Cl.$^4$ ............................................. A01M 1/20

[52] U.S. Cl. ...................................... 43/124; 43/131; 427/256; 427/288; 428/195; 428/211

[58] Field of Search ...................... 428/195, 196, 211; 427/256, 288; 43/124, 131; 424/6, 29

[56] References Cited

U.S. PATENT DOCUMENTS 4,103,450 8/1978 Whitcomb ............................. 43/131

*Primary Examiner*—James J. Bell
*Attorney, Agent, or Firm*—Felfe & Lynch

[57] ABSTRACT

Insecticidal compositions consisting of a carrier material and having at least one insecticidal substance deposited thereon, where the carrier material includes zones free from insecticidal substance and zones containing insecticidal substance, the division into said zones being produced by printing methods.

9 Claims, No Drawings

INSECTICIDAL COMPOSITIONS

This is a continuation of application Ser. No. 06/901,019, filed Aug. 28, 1986, now abandoned.

This invention relates to insecticidal compositions for the control of textile pests and to methods of preparing such compositions.

BACKGROUND OF THE INVENTION

Insecticidal compositions consisting essentially of a carrier material and insecticidal substances applied to this carrier material are used to combat various stages in the development of textile pests. The most serious textile pests are the clothes moth, the fur moth, the larder beetle and the fur beetle.

Insecticidal papers are the most widely used mothproofing compositions. These are divisible elongate strips which are hung in a clothes closet or placed as individual sheets in a dresser drawer. The insecticidal substance evaporating from the carrier (in this case paper) serves to control the textile pests.

After 6 to 12 months the efficacy of the paper has dwindled to such an extent that it has to be renewed.

Mothproofing papers are produced by two different industrial scale processes, namely the impregnating process and the coating process.

In the impregnating process, a length of absorbent paper is unwound from a roll, passed through a bath of insecticidal substance, and dried in a drying tunnel. The paper impregnated in this way is then cut into separate ready-to-use strips.

In the coating process, the insecticidal substance is incorporated into the aqueous paste of a dispersion dye. The resulting insecticidal substance-containing paste is painted onto one or both sides of a length of paper as it is being unwound from a roll, then dried in a drying tunnel, rolled up again and then once again unrolled and divided into separate ready-to-use strips.

Since the insecticidal substance is uniformly distributed over the entire surface of the carrier paper in the mothproofing papers produced by the impregnating and coating methods, the quantity of insecticidal substance applied per unit surface area cannot be freely selected for a given total surface area of a strip of mothproofing paper. Furthermore, the user cannot judge whether the insecticidal substance has diffused out of the mothproofing paper and if the mothproofing paper needs renewing.

OBJECTS OF THE INVENTION

It is an object of the present invention to provide mothproofing compositions which avoid the above-mentioned disadvantages in manufacture, use and range of applications, and methods of preparing them.

Other objects and advantages of the instant invention will become apparent as the description thereof proceeds.

DESCRIPTION OF THE INVENTION

The above object is achieved according to the present invention with an insecticidal composition consisting essentially of a carrier material and one or more insecticidal substances, characterized in that the carrier material comprises zones containing insecticidal substance and zones free from insecticidal substance.

The insecticidal substance used may, in theory, be any insecticidal substance which has a sufficiently high vapor pressure at room temperature to reach a concentration sufficient to kill textile pests in enclosed spaces, that is, under the conditions of use which generally apply to mothproofing papers or the like.

Particular mention should be made of the insecticidal substances listed below, which may be used by themselves or in combination with other insecticidal substances having the properties referred to in the preceding paragraph:

Chlorinated hydrocarbons such as
  lindane or methoxychlor;
Phosphoric acid esters such as
  chlorpyrifos, chlorpyrifos-methyl or dichlorvos;
Pyrethroids such as
  vaporthrin (emphenthrin), permethrin, bioresmethrin, bioallethrin, kadethrin, decis, cyfluthrin or fenfluthrin.

Preferably, the following amounts of insecticidal substance are used:

Chlorinated hydrocarbons: 5–15 $g/m^2$
Phosphoric acid esters: 5–10 $g/m^2$
Pyrethroids: 0.2–5 $g/m^2$ As indicated above, the insecticidal substances may be used by themselves or in combination with other insecticidal substances. Consequently, the amount to be applied to the carrier material may vary accordingly.

The following carrier materials may be used: Paper, cardboard plastic films, textile materials or non-woven materials.

The insecticidal substance is preferably applied to the carrier material by a printing method.

The term "printing method" as used herein covers all processes in which the insecticidal substance is applied to the carrier material in the form of a surface pattern.

In principle, all printing methods such as screen printing, flexoprinting, intaglio printing or contact-free printing methods such as ink jet printing are suitable.

The surface pattern of insecticidal substance on the carrier material may also be applied by means of spray jets, where the areas containing insecticidal substance and those free from insecticidal substance according to the invention are produced on the carrier material by pulsation and/or deflection of the jet.

The present invention thus also includes processes for preparing mothproofing compositions by means of printing methods.

The choice of a suitable printing method depends on the nature of the carrier material. When paper, cardboard or a plastic film is used, intaglio printing is preferred; and when textile material and non-woven materials are used, screen printing is preferred.

The insecticidal ingredient may be applied to the carrier material after dilution with a suitable solvent to form a paste, suspension or solution or, if it is already in the form of a liquid or paste, it may also be used undiluted.

By using printing methods to apply the insecticidal ingredient to the carrier material, it is possible to reduce the amount of solvent to a minimum, so that the printed carrier material does not have to be subjected to special heat treatment.

This feature is of critical importance and a significant advance over the methods of producing mothproofing papers heretofore used. In the impregnating method and coating process, sufficient solvent must be used to impregnate the carrier material completely or coat it over its entire surface. In both processes, the solvent has to be removed afterwards by drying.

Since the drying step is not required in the manufacturing process according to the present invention, the losses of insecticidal substance and deterioration in the quality of the insecticidal substance do not occur. The division of the mothproofing composition into zones containing insecticidal substance and zones free from insecticidal substance, which is achieved by the printing method which is used according to the present invention, has a number of advantages:

The zones containing insecticidal substance and those free from insecticidal substance are arranged on the carrier material in such a way that the waste material cut off during packaging is free from insecticidal substance. The waste material can therefore be recycled without any special precautions.

Different insecticidal substances or adjuvants which are not chemically compatible with each other can be applied to the carrier material by separating them spatially.

The areas on the carrier material containing insecticidal substance are easily distinguishable from those of the carrier material free from insecticidal substance by the difference in background color, usually a deepening of color by about 2 tones. The dwindling of the insecticidal activity of the insecticidal paper is indicated by the disappearance of this color difference.

By imprinting specific areas of the carrier material with insecticidal substance, optionally with an increased surface concentration and/or with a different adjuvent corresponding to the vaporization characteristics of the insecticidal substance, it is possible to produce test areas in which a change in color compared with an unprinted area indicates to the user that the insecticidal activity is diminishing.

A further advantage of the process of the instant invention is that the insecticidal substance can be accurately metered by means of precisely engraved or etched printing rollers or printing plates. As a result, small quantities of modern, highly effective insecticides can be used economically.

The total quantity of active substance applied to the carrier material per unit area of the insecticidal composition can be controlled by means of a number of variables:

(a) By the ratio of surface area free from insecticidal substance to surface area containing insecticidal substance;

(b) By the quantity of insecticidal substance applied per unit area to the insecticidal substance-containing zone, which is controllable by means of the concentration of the solution of insecticidal substance; in printing processes it is controllable by varying the depth of etching of the printing roller or printing plate; and in spray processes it is controllable by the duration of the spraying pulse per unit area, etc.

As shown in Example 3 below, an increase in the quantity of insecticidal substance applied per unit area containing insecticidal substance results in an improvement in the long-term effect.

Furthermore, the long-term effect of the insecticidal composition imprinted with insecticide can be improved by coating it with a plastic film using known methods.

The division of the insecticidal composition of the instant invention into zones free from insecticide and zones containing insecticide thus applies both to the as yet unpackaged carrier material containing insecticide and to the finished end product. Both of these advantageous effects may be used independently of each other.

The division into zones containing insecticide and zones free from insecticide which is achieved by printing methods is naturally evened out by diffusion during storage of the insecticidal composition so that the boundary between the zones containing insecticide and the zones free from insecticide corresponds to a more or less steeply descending concentration gradient.

The following examples illustrate the present invention and will enable others skilled in the art to understand it more completely. It should be understood, however, that the invention is not limited solely to the particular examples given below.

Examples 1 and 2 give the process parameters for printing a carrier paper of a specific weight per unit area with two different insecticidal substances.

Example 3 shows the improvement in the long-term effect achieved by varying the quantity of insecticidal substance applied per unit area.

EXAMPLE 1

| Liquid insecticidal substance (vaporthrin) | |
|---|---|
| Carrier material: special printing paper | 100 g/m$^2$ |
| Quantity of vaporthrin applied by printing: | 2.5 g/m$^2$ |
| Quantity of ink applied by printing: | 2.0 g/m$^2$ |
| Quantity of perfume applied by printing: | 0.5 g/m$^2$ |
| Intaglio printing press with etched special roller (grid 100, depth of etching 30 my). | |

EXAMPLE 2

| Solid insecticidal substance (chlorpyriphos) | |
|---|---|
| Carrier material: special printing paper | 100 g/m$^2$ |
| Quantity of chlorpyriphos applied by printing (50% by weight solution of chlorpyriphos in ethyl acetate) | 12 g/m$^2$ |
| Quantity of ink applied by printing: | 2 g/m$^2$ |
| Quantity of perfume applied by printing: | 1 g/m$^2$ |
| Intaglio printing press with etched special roller (grid 50, depth of etching 50 my). | |

EXAMPLE 3

Improvement in long-term effect achieved by increasing the quantity of insecticidal substance per unit area. 400 mg of vaporthrin were applied by printing to pieces of paper measuring 100 and 50 cm$^2$, and the imprinted pieces of paper were hung up freely at room temperature. The quantity of insecticide given off was determined by weighing at intervals of 10 days.

The accompanying drawing shows the amount of vaporthrin (in mg) given off over a period of 90 days.

Curve ① 400 mg on 100 cm$^2$ paper (weight per unit area 100 g/m$^2$)=4 mg/cm$^2$ Curve ② 400 mg on 50 cm$^2$ paper (weight per unit area 100 g/m$^2$)=8 mg/cm$^2$ While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An insecticidal composition consisting essentially of a sheet of carrier material divisible into segments thereof by cutting, discrete deposits of at least one insecticidal substance printed onto a surface of said sheet of carrier material, and surface areas devoid of deposits of insecticidal substance spatially separating said discrete insecticidal deposits from each other, whereby waste material produced by cutting individual insecticidal segments from said sheet is devoid of insecticidal substance.

2. A composition of claim 1, where said carrier material is paper.

3. A composition of claim 1, where said carrier material is a plastic film, textile material, cardboard or nonwoven material.

4. A composition of claim 1, where said insecticidal substance is selected from the group consisting of lindane, methoxychlor, chlorpyrifos, chlorpyrifosmethyl, dichlovos, vaporthrin, permethrin, bioresmethrin, bioallethrin, kadethrin, decis, cyfluthrin and fenfluthrin.

5. A composition of claim 1, where said carrier material having insecticide deposited thereon is coated with plastic material, whereby its length of effective duration of activity is increased.

6. The method of preparing an insecticidal composition of claim 1, which comprises depositing a liquid, paste or suspension containing an insecticidal substance on said carrier material by printing methods.

7. The method of claim 6, where said carrier material is paper.

8. The method of claim 6, where said carrier material is a plastic film, textile material, cardboard or nonwoven material.

9. The method of claim 6, where said insecticidal substance is selected from the group consisting of lindane, methoxychlor, chlorpyrifos, chlorpyrifosmethyl, dichlorvos, vaporthrin, permethrin, bioresmethrin, bioallethrin, kadethrin, decis, cyfluthrin and fenflurthrin.

* * * * *